United States Patent [19]
Phillips et al.

[11] Patent Number: 5,495,044
[45] Date of Patent: Feb. 27, 1996

[54] INHIBITORS OF KYNURENINASE

[75] Inventors: Robert S. Phillips; Lakshmi V. Cyr, both of Athens, Ga.

[73] Assignee: University of Georgia Research Foundation, Inc., Athens, Ga.

[21] Appl. No.: 145,074

[22] Filed: Oct. 29, 1993

Related U.S. Application Data

[63] Continuation-in-part of Ser. No. 137,100, Oct. 18, 1993, Ser. No. 840,408, Feb. 24, 1992, abandoned, and Ser. No. 689,705, Apr. 18, 1991, Pat. No. 5,254,725.

[51] Int. Cl.$^6$ ..................... C07C 229/36; A61K 31/195
[52] U.S. Cl. .................. 562/449; 562/437; 562/444
[58] Field of Search .................. 562/449, 437, 562/444; 514/564, 563, 567

[56] References Cited

U.S. PATENT DOCUMENTS

| | | | |
|---|---|---|---|
| 4,293,569 | 10/1981 | Haugwitz et al. | 424/300 |
| 4,332,813 | 6/1982 | Firestone | 424/273 R |
| 4,609,673 | 9/1986 | Eggerer et al. | 514/542 |
| 4,730,008 | 3/1988 | Skidmore et al. | 514/605 |
| 5,254,725 | 10/1993 | Phillips et al. | 562/444 |

OTHER PUBLICATIONS

Kolb, M. and Neises, B. (1986) "Synthesis of Fluorinated α-Amino Ketones. Part II: α-Acylaminoalkyl α', α'-Difluoroalkyl Ketones"; *Tetrahedron Lett.* 37 (vol. 27): 4437–4440.

Dua, R. K. et al. (1993) "S-Aryl-L-cystein S,S-Dioxides: Design, Synthesis, and Evaluation of a New Class of Inhibitors of Kynureninase"; *J. Am. Chem. Soc.* 115: 1264–1270.

Dua et al. (1992) Abstract entitled "S-Aryl-L-Cystein Sulfone: A New Class of Mechanism Based Inhibitors of Kynureninase," Abstracts, *Amer. Chem. Soc.* vol. 203 (Apr.), 119 (MEDI).

Phillips & Dua (1991), "Stereochemistry and Mechanism of Aldol Reactions Catalyzed by Kynureninase", Abstracts, *Amer. Chem. Soc.* vol. 201 (Apr.) 283 (ORGN).

Phillips & Dua (1991), "Stereochemistry and Mechanism of Aldol Reactions Catalyzed by Kynureninase", *J. Amer. Chem. Soc.* 113: 7385–7388.

Kibat et al. (1990), "Enzymatically Activated Microencapsulated Liposomes can Provide Pulsatile Drug Release", *The FASEB Journal*, 4: 2533–2539.

Crescenzi et al. (1990), "Synthesis and Reactivity of Cyclic Quinonimines of the 2H–1, 4–Benzothiazine Series", *Gazzetta Chimica Italiana* 120: 21–24.

J. P. Whitten et al. (1989), "A Convenient Synthetic Access to β, β-Difluoro-α-Amino Acids. Application to the Synthesis of a Potential Inhibitor of Kynureninase", *Tetrahedon Letters* 30: 3649–3652.

Blagbrough et al. (1988), "Inhibition of Rat Renal C–S Lyase: Assessment Using Kidney Slice Methodology," *Drug Metab. Drug Interact* 6: (3–4) 303–316.

Blagbrough et al. (1988), "Substrates for Rat Renal C–S Lyase," *J. Pharm. Pharmacol.* 41(suppl.): 148.

Vamvakas et al. (1988), "Bacterial cysteine Conjugate β–Lyase and the Metabolism of Cysteine S–Conjugates: Structural Requirements for the Cleavage of S–Conjugates and the Formation of Reactive Intermediates", *Chem. Biol. Interact* 65: 59–71.

Tarzia et al. (1988) "Alkyl 2–(Diphenylmethyleneamino) Acrylates in the Synthesis of α–Amino Acids", *Synthesis* 7: 514–517.

J. L. Stevens (1985), "Isolation and Characterization of a Rat Liver Enzyme with Both Cysteine Conjugate β–Lyase and Kynureninase Activity", *J. Biol. Chem* 260: 7945–7950.

Palcic et al. (1985), "Stereochemistry of the Kynureninase Reaction", *J. Biol. Chem.* 260: 5248–5251.

G. A. Flynn et al. (1984), *Tettrahedon Lett.* 25: 2655–2658.

G. M. Kishore (1984), "Mechanism–based Inactivation of Bacterial Kynureninase by β–Substituted Amino Acids", *J. Biol. Chem.* 259: 10669–10674.

K. Tanizawa et al. (1979), "The Mechanism of Kynurenine Hydrolysis Catalyzed by Kynureninase", *J. Biochem.* 86: 1199–1209.

K. Soda and K. Tanizawa (1979), "Kynureninase: Enzymological Properties and Regulation Mechanism", *Advances Enzym.* 49: 1–40.

F. McCapra and Z. Razavi (1976), "Biosynthesis of Luciferin in *Pyrophorus Pellucens*", *J. Chem. Soc.* 5: 153–154.

(List continued on next page.)

*Primary Examiner*—Paul F. Shaver
*Assistant Examiner*—Barbara S. Frazier
*Attorney, Agent, or Firm*—Greenlee and Winner

[57] ABSTRACT

The present invention provides inhibitors of kynureninase having the formula

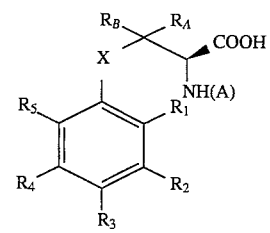

where X is CO or CHOH; $R_A$ and $R_B$, independently of one another, are H, a halogen, a halovinyl group, or a small alkyl or haloalkyl group having one to three carbon atoms; A is a H or an acetyl group; $R_1$ is H, $NH_2$, $NR_6R_7$, $NO_2$, halogen, $CF_3$ or a small alkyl group having from one to three carbon atoms, wherein: $R_6$ and $R_7$, independently of one another, are H, a formyl group or a small alkyl group having from one to three carbon atoms with the exception that only one of $R_6$ or $R_7$ can be a formyl group; $R_2$ is OH, H, halogen, $CF_3$ or a small alkyl group having from one to three carbon atoms; and $R_3$, $R_4$ and $R_5$, independently of one another, are H, halogen, $CF_3$, $NO_2$, $NH_2$, or small alkyl group having from one to three carbon atoms, and with the proviso that when X=CO, neither $R_A$ nor $R_B$ can be $CF_3$. In compounds of this formula in which X is CHOH, those having the (αS,γS) configuration or the (αR,γR) configuration when $R_A$ or $R_B$ is a hydrogen, are more potent inhibitors of kynureninase. Inhibitors of mammalian kynureninase are of particular use in therapy for certain neurological disorders.

18 Claims, No Drawings

OTHER PUBLICATIONS

T. L. Gilchrist et al. (1979), "Ethyl 3-Bromo-2-hydroxyiminopropanoate, a Reagent for the Preparation of Ethyl Esters of α-Amino Acids", *J. C. S. Chem. Comm.* 1089–1090.

A. P. Damoglou et al. (1971), "The Hydrolysis by Thermolysin of Dipeptide Derivatives that Contain Substituted Cysteine", *Biochem. J.* 123: 379–384.

Mikheeva et al. (1968) *Chem. Abstracts* 69: 18764m.

L. Goodman et al. (1958), "Potential Anticancer Agents v. Some Sulfur–Substituted Derivatives of Cysteine", *J. Org. Chem.* 23: 1251–1257.

O. Hayaishi (1955) in "A Symposium on Amino Acid Metabolism" (W. D. McElroy and H. B. Glass, eds.) *Johns Hopkins Press*, Baltimore pp. 914–929.

O. Wiss and H. Fuchs (1950) *Experientia* 6: 472–473.

Tolosa et al. (1968) *Chem. Abstracts* 70(1): 482d and *English Abstract of Tolosa et al.* (1968) *Mol. Biol.* 2(5): 769–777 (in Russian).

INHIBITORS OF KYNURENINASE

This invention was made through a grant from the National Institutes of Health. The United States Government has certain rights in this invention. This application is a continuation-in-part of U.S. patent application Ser. No. 08/137,100, which is the National Phase of PCT/US92/03198 (international filing date Apr. 17, 1992) filed on Oct. 18, 1993; U.S. Ser. No. 07/840,408, filed Feb. 24, 1992, now abandoned, which is incorporated by reference herein; and U.S. Ser. No. 07/689,705, filed Apr. 18, 1991, and issued as U.S. Pat. No. 5,254,725 on Oct. 19, 1993.

BACKGROUND OF THE INVENTION

Kynureninases are a group of pyridoxal-5'-phosphate dependent enzymes which catalyze the hydrolytic $\beta,\gamma$-cleavage of aryl-substituted $\alpha$-amino-$\gamma$-keto acids, particularly L-kynurenine or 3-hydroxy-L-kynurenine to give L-alanine and anthranilic acid or 3-hydroxyanthranilic acid, respectively (see: K. Soda and K. Tanizawa (1979) *Advances Enzym.* 49:1–40). Kynureninase is involved in the microbial catabolism of L-tryptophan via the aromatic pathway. In plants and animals, a kynureninase is required in tryptophan catabolism and for NAD biosynthesis via quinolinic acid. Quinolinic acid is a relatively toxic metabolite, and in particular, it is a potent neurotoxin which has been implicated in the etiology of neurological disorders, including epilepsy and Huntington's chorea (R. Schwarcz et al. (1988) *Proc. Natl. Acad. Sci. USA* 85:4079; M. F. Beal et al. (1986) *Nature* 321:168–171; S. Mazzari et al. (1986) *Brain Research* 380:309–316; H. Baran and R. Schwarcz (1990) *J. Neurochem.* 55.:738–744). It has been found that the activity of this pathway for tryptophan matabolism in mammals is elevated by interferon and by transient ischemia (Ozaki et al. (1988) *Proc. Natl. Acad. Sci. USA* 85: 1242–1246; Saito et al. (1993) *J. Neurochem.* 60: 180). The resultant increase in brain and/or serum quinolinate may result in neuropathology. Inhibitors of kynureninase are thus important targets for treatment of neurological disorders, including strokes. High levels of nicotinylalanine, a weak inhibitor of kynureninase in vitro, have been shown to inhibit the accumulation of quinolinic acid in vivo, following administration of bacterial endotoxins to rats (Moroni et al. (1991) *J. Neurochem.* 57: 1630).

L-kynurenine (which can also be designated $\alpha,2$-diamino-$\gamma$-oxobenzenebutanoic acid) is the preferred substrate of bacterial kynureninase, which is exemplified by that of *Pseudomonas fluorescens* (O. Hayaishi and R. Y. Stanier (1952) *J. Biol. Chem.* 195:735–740). The kynureninase of tryptophan metabolism in plants and animals has a somewhat different substrate specificity with 3-hydroxy-L-kynurenine (which can be designated $\alpha,2$-diamino-3-hydroxy-$\gamma$-oxobenzenebutanoic acid) being the preferred substrate (Soda and Tanizawa (1979) supra).

The mechanism of kynureninases has been the subject of considerable interest due to the unique nature of this pyridoxal-5'-phosphate dependent reaction. Mechanisms based on redox reactions (J. B. Longenecker and E. E. Snell (1955) *J. Biol. Chem.* 213:229–235) or transamination (C. E. Dalgleish et al. (1951) *Nature* 168:20–22) have been proposed. More recently mechanisms involving either a nucleophilic mechanism with an "acyl-enzyme" intermediate (C. Walsh (1979) "Enzymatic Reaction Mechanisms" W. H. Freeman and Co., San Francisco, p. 821; M. Akhtar et al. (1984) "The Chemistry of Enzyme Action," *New Comprehensive Biochemistry*, Vol. 6 (M. I. Page, ed.) Elsevier, New York, p.821) or a general base-catalyzed mechanism (K. Tanizawa and K. Soda (1979) *J. Biochem.* (Tokyo) 86:1199–1209) have been proposed. Kynureninase is now recognized as one of only a few pyridoxal-5'-phosphate (PLP) dependent enzymes which catalyze reactions with electrophilic substitution at the $\beta$-carbon. In contrast, many PLP-dependent enzymes catalyze reactions involving nucleophilic substitution at the $\beta$-carbons of amino acids. The unique feature of the proposed mechanism of kynureninase is the resonance stabilized alanine $\beta$-carbanion intermediate generated by the retro-Claisen cleavage of the gem-diol of kynurenine [Phillips and Dua (1991) *J. Am. Chem. Soc.* 113: 7385; Dua et al. (1993) *J. Am. Chem. Soc.* 115: 1264].

In addition to the physiological reaction, kynureninase has been shown to catalyze an aldol-type condensation of benzaldehyde with incipient L-alanine formed from L-kynurenine to give $\alpha$-amino-$\gamma$-hydroxy-$\gamma$-phenylbutanoic acid (G. S. Bild and J. C. Morris (1984) *Arch. Biochem. Biophys.* 235:41–47). The stereochemistry of the product at the $\gamma$-position was not determined, although the authors suggested that only a single isomer was formed.

J. L. Stevens (1985) *J. Biol. Chem* 260:7945–7950 reports that rat liver kynureninase displays cysteine conjugate $\beta$-lyase activity. This enzyme activity is associated with cleavage of S-cysteine conjugates of certain xenobiotics to give pyruvate, ammonia and a thiol, for example, cleavage of S-2-(benzothiazolyl)-L-cysteine to give 2-mercaptobenzothiazole, pyruvate and ammonia. More recently, I. S. Blagbrough et al. (1990) *Toxicol. Lett* 53(1–2):257–259 (*Chem. Abstract* 114(9):77537k) report that cysteine conjugate $\beta$-lyase (C-S-lyase) is a member of a family of transaminases and aminotransferases and that C-S lyase is a glutamine transaminase K. The reference discusses structure-activity relations displayed by C-S-lyases. C-S-lyases are distinguishable from kynureninase but exhibit overlapping activities.

Several reports concerning the relative reactivities of kynurenine analogs with bacterial kynureninase or rat liver kynureninase are summarized in Soda and Tanizawa (1979) supra. Tanizawa and Soda (1979) supra reported that a number of ring substituted L-kynurenines, namely: 3-hydroxy-, 5-hydroxy-, 5-methyl-, 4-fluoro-, and 5-fluoro-L-kynurenine were substrates of kynureninase of *P. fluorescens*. These authors also reported that dihydrokynurenine (called $\gamma$-(o-aminophenyl)-L-homoserine therein) was a substrate for that kynureninase, yielding o-aminobenzaldehyde and L-alanine. The $K_m$ of dihydrokynurenine was reported to be 67 $\mu$M compared to a $K_m$ of 35 $\mu$M for L-kynurenine and 200 $\mu$M for 3-hydroxy-L-kynurenine. N'-formyl-L-kynurenine and $\beta$-benzoyl-L-alanine were likewise reported to be substrates (with $K_m$=2.2 mM and 0.16 mM, respectively) for the bacterial kynureninase. Tanizawa and Soda measured relative reactivity as relative amount of L-alanine formed.

O. Hayaishi (1955) in "A Symposium on Amino Acid Metabolism" (W. D. McElroy and H. B. Glass, eds.) Johns Hopkins Press, Baltimore, pp. 914–929, reported that 3-hydroxy- and 5-hydroxy-L-kynurenine, $\beta$-benzoyl-L-alanine and $\beta$-(o-hydroxybenzoyl)-L-alanine were substrates for the bacterial enzyme, but that N'-formyl-L-kynurenine was not a substrate. O. Hayaishi measured relative reactivities by determining the amounts of substrate hydrolyzed.

Tanizawa and Soda (1979) supra reported that S-benzoyl-L-cysteine, L-asparagine and D-kynurenine were not substrates of kynureninase, while O. Hayaishi (1955) Supra reported that $\beta$-(p-aminobenzoyl)-L-alanine, $\beta$-(o-nitrobenzoyl)-L-alanine, β-(m-hydroxybenzoyl)-L-alanine, 3-methoxy-L-kynurenine, β-benzoylpropanoic acid, and β-(o-aminobenzoyl)propanoic acid do not react with bacterial kynureninase. Kynureninase is reported to act only on L-amino acids (M. Moriguchi et al. (1973) *Biochemistry* 12:2969–2974).

O. Wiss and H. Fuchs (1950) *Experientia* 6:472 (see: Soda and Tanizawa (1979) supra) reported that 3-hydroxy-L-kynurenine, L-kynurenine, β-benzoyl-L-alanine, γ-phenyl-L-homoserine, γ-methyl-L-homoserine, 2-aminolevulinic acid and α-amino-γ-hydroxypentanoic acid reacted with rat liver kynureninase to produce alanine, while β-(o-nitrobenzoyl)-L-alanine did not.

G. M. Kishore (1984) *J. Biol. Chem.* 259:10669–10674 has reported that certain β-substituted amino acids are mechanism-based inactivators of bacterial kynureninase. Several β-substituted amino acids including: β-chloro-L-alanine, O-acetyl-L-serine, L-serine O-sulfate, S-(2-nitrophenyl)-L-cysteine (called S-(o-nitrophenyl)-L-cysteine, therein) and β-cyano-L-alanine inactivated kynureninase. These β-substituted amino acids react with kynureninase to give pyruvate and ammonia. Amino acids with good leaving groups at the β-carbon, such as β-chloroalanine, were shown to act as irreversible inactivators of kynureninase from *P. marginalis*. However, these compounds have high $K_i$ values and inactivate a large number of PLP-dependent enzymes. S-(2-nitrophenyl)-L-cysteine, which is not a β-substituted amino acid, was described as the "most efficient suicide substrate at low concentrations" with a $K_i$ of 0.1 mM.

Bacterial kynureninase is also strongly inhibited by o-aminobenzaldehyde ($K_i$=6.5 μM, non-competitive inhibition). Several other aromatics having "a carboxyl group on the benzene ring and an amino group at the ortho-position" including o-aminoacetophenone, anthranilic acid o-nitrobenzaldehyde and benzaldehyde were described as inhibitors (Tanizawa and Soda (1979) supra). It was suggested that inhibition relates to binding of the formyl group to the portion of the enzyme that serves as a binding site for the γ-carboxyl of kynurenine. Anthranilate and 3-hydroxyanthranilate, the products of the kynureninase reaction, were also reported to inhibit the enzyme (Takeuchi et al. (1980) *J. Biochem.* (Tokyo) 88:987–994).

Blagbrough, I. S. et al. (1988) *Drug Metab. Drug Interact* 6(3–4):303–316 in *Chem. Abstracts* 112(19):174617c report on inhibition of rat renal C-S lyase by certain cysteine conjugates. Certain S-(nitro-substituted phenyl)-L-cysteines and N-acetyl-S-(nitro-substituted phenyl)-L-cysteines were reported to inhibit C-S lyase as measured by a kidney slice methodology. The nitrophenyl cysteine conjugates: S-(2-nitrophenyl)-L-cysteine, S-(4-nitrophenyl)-L-cysteine, S-(2,6-dinitrophenyl)-L-cysteine, N-acetyl-S-(3,4-dinitrophenyl)-L-cysteine, N-acetyl-S-(2,6-dinitrophenyl)-L-cysteine and N-acetyl-S-(2-chloro-4-nitrophenyl)-L-cysteine are reported to inhibit C-S layse.

Vamvakas et al. (1988) *Chem. Biol. Interact* 65:59–71 in *Chem. Abstracts* 109(7):50020w refers to the cysteine conjugate β-lyase-mediated metabolism of certain cysteine conjugates including S-benzyl-L-cysteine, which was reported to be cleaved to give pyruvate. The reference notes that aminooxyacetic acid is an inhibitor of the β-lyase.

Tolosa et al. (1968) *Mol. Biol.* 2(5):769–777 [in Russian] in *Chem. Abstracts* 70(1):482d reported that cysteine lyase was significantly inhibited by $H_2NOH$ and its O-substituted derivatives and that aminooxyacetic acid was the most inhibitory derivative tested.

J. P. Whitten et al. (1989) *Tetrahedron Letts.* 30:3649–3652 reported the synthesis of 2,2-difluoro-α-benzoyl alanine (α-amino-β,β-difluoro-γ-oxobenzene butanoic acid) which is said to be a "potential new inhibitor of kynureninase." Fluoroketone-containing peptides are described as capable of forming stable hydrates or hemiketals which are "thought to inhibit" proteolytic enzymes as analogs of a tetrahedral transition state. The difluoro compound is described as a competitive inhibitor of kynureninase, but no details of this inhibition are given in the reference.

The present work is based on a reexamination of the mechanism of kynureninase catalysis, in particular, through an investigation of the stereospecificity of the retro-aldol reaction catalyzed by the enzyme. During the course of this work, the reactivity of dihydrokynurenine with kynureninase was found to be significantly different than had previously been reported. The result of these mechanism and reactivity studies was the identification of a class of potent kynureninase inhibitors. The present invention provides kynureninase inhibitors which are designed to be "transition-state analogue" inhibitors.

SUMMARY OF THE INVENTION

It is an object of the present invention to provide means and compositions for inhibition of kynureninase. In the methods of this invention a kynureninase is contacted with an inhibitory amount of a kynureninase inhibitor of this invention. The kynureninase inhibitors of this invention are amino acid derivatives of the formula:

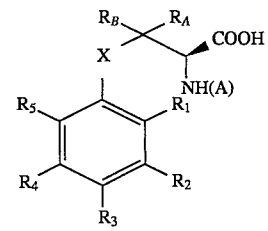

wherein the stereochemical configuration at the α-carbon is as indicated in Formula I (and is the same configuration as the α-carbon in L-kynurenine); where X is CO or CHOH; $R_A$ is a haloalkyl or halovinyl group having one to three carbon atoms and $R_B$ is H, or halogen, or a small alkyl or haloalkyl, or halovinyl group each having one to three carbon atoms; A is H or an acetyl group; $R_1$ is H, halogen, $NH_2$, $NR_6R_7$, $NO_2$, $CF_3$, or a small alkyl having from one to three carbon atoms; with $R_6$ and $R_7$, independently of one another, being H, a small alkyl group having from one to three carbon atoms, or COH wherein only one of $R_6$ or $R_7$ can be COH; $R_2$ is OH, H, halogen, $CF_3$ or a small alkyl having from one to three carbon atoms; and $R_3$, $R_4$ and $R_5$, independently of one another, are H, OH, halogen, CF3, $NO_2$, $NH_2$, or a small alkyl group having from one to three carbon atoms, with the proviso that when X=CHOH, neither $R_A$ nor $R_B$ can be $CF_3$. Within the context of kynureninase-inhibiting compounds, halogens can be fluorine or chlorine, among others. Generally fluorine is preferred to chlorine. Halovinyl groups can include among others $CF=CH_2$, $CF—CF_2$, $CH=CF(CH_3)$, or $CF=CF(CF_3)$, $CF=CF(CH_3)$, $CH=CF(CF_3)$. Haloalkyl groups can include, among others, $CF_3$, $CHF_2$, $CH_2F$, $CH_2CF_3$, $CH_2CHF_2$, $CH_2$, $CH_2$ F, $CH_2CH_2CF_3$, $CH_2CH_2CHF_2$ and $CH_2CH_2CH_2F$. Haloalkyl groups can also be one of $CF_3$, $CHF_2$, $CH_2F$, $CH_2CF_3$, $CH_2CH_2F$ and $CH_2CHF_2$. Alternatively, haloalkyl groups can include $CF_3$, $CHF_2$, $CH_2F$, $CHFCH_3$, $CHFCH_2CH_3$, $CF_2CH_2CH_3$, $CHFCH_2CH_3$ and the like, where there is at least one F on the carbon covalently bound to the β-carbon. Alternatively, a haloalkyl group can be one of $CF_3$, $CH_2F$ and $CHF_2$. The haloalkyl groups set forth above can also further include the chlorinated analogs of any of the foregoing.

For inhibition of kynureninase, X can be CO or CHOH, and it is generally preferred that $R_1$ is $NH_2$. To achieve irreversible inhibition of kynureninase, it is preferred that the $R_A$ group have a halogen on the carbon bonded to the β-carbon of the inhibitor. Preferably the halogen is F. When X is CO, it is contemplated that $R_A$ can be a haloalkyl group, and $R_B$ can also be a haloalkyl or a halovinyl group. Within this context, halogens can be fluorine or chlorine, among others. Generally fluorine is preferred to chlorine. Halovinyl groups can include $CF=CH_2$ and $CF=CF_2$. Haloalkyl groups can include, among others $CF_3$, $CHF_2$, $CH_2F$, $CH_2CF_3$, $CH_2CHF_2$, $CH_1$, $CH_2F$, $CHFCH_3$, $CF_2CH_3$, $CHFCHF_2$, $CF_2$, $CHF_2$, $CHFCH_2F$, $CF_2CH_2F$, $CHFCF_3$, $CF_2CF_3$, $CH_2CH_2CF_3$, $CH_2CH_2CHF_2$ and $CH_2CH_2CH_2F$. Haloalkyl groups can also be one of $CF_3$, $CHF_2$, $CH_2F$, $CH_2CF_3$, $CHFCH_3$, $CF_2CH_3$, $CHFCHF_2$, $CF_2$, $CHF_2$, $CHFCH_2F$, $CF_2CH_2F$, $CHFCF_3$, $CF_2CF_3$, as well as $CHFCH_2CH_3$, $CF_2CH_2CH_3$, $(CHF)_2CH_3$, $CH_2CHFCH_3$, $CF_2CHFCH_3$, $CHFCF_2CH_3$, $(CF_2)_2CH_3$, $CHFCH_2CF_3$, $CF_2CH_2 CF_3$, $(CHF)_2CF_3$, $CHFCF_2CF_3$, $(CF_2)_2CF_3$, and so a haloalkyl or alkyl group may further include $(CH_2)_2CF_3$, $CH_2CH_2F$ and $CH_2CHF_2$. Alternatively, a haloalkyl group can be one of $CF_3$, $CH_2F$ and $CHF_2$. The haloalkyl and halovinyl groups set forth above can also further include the chlorinated analogs of any of the foregoing. Where X is CHOH, one or both of $R_A$ and $R_B$ cannot be $CF_3$. It is preferred that where $R_A$ or $R_B$ is a haloalkyl group, the carbon of the haloalkyl group bound to the β-carbon will have at least one halogen bound to it. $R_1$–$R_5$ can be any of those set forth above. $R_1=NH_2$ is a preferred substitutent.

Inhibitors useful in the methods of this invention include the compounds of formula I in which the halogen of $R_1$–$R_5$ is fluorine, $R_2$ is H or OH, $R_1$ is H or $NH_2$, and $R_A$, $R_B$, $R_4$ and $R_5$ are H or fluorine. Useful inhibitors also include those in which $R_3$ is H, $NH_2$, $NO_2$ or fluorine, with H or fluorine preferred. More preferred inhibitors are those in which $R_1$ is $NH_2$ and $R_A$, $R_B$, $R_3$, $R_4$ and $R_5$ are H.

For inhibition of bacterial kynureninase, it is preferred that $R_2$ is H. For inhibition of plant and animal kynureninase, it is preferred that $R_2$ is OH.

Subsets of inhibitors useful in the methods of this invention are compounds of formula I in which:

X=CO and all of $R_A$, $R_B$, A, $R_1$–$R_5$ are as broadly defined above;

X=CHOH and all of $R_A$, $R_B$, A, $R_1$–$R_5$ are as broadly defined above, but with neither $R_A$ nor $R_B$ being $CF_3$;

X=CO, $R_A$ is haloalkyl having one to three carbon atoms, and all of $R_A$, $R_B$, A, $R_1$–$R_5$ are as broadly defined above;

X=CHOH, $R_A$ is haloalkyl having one to three carbon atoms, and all of $R_A$, $R_B$, A, $R_1$–$R_5$ are as broadly defined above;

X=CO, $R_A$=haloalkyl or halovinyl having one to three carbon atoms, $R_B$ is as defined broadly above, $R_1$ is $NH_2$ and A, $R_2$–$R_5$ are all H;

X=CO, $R_A$=haloalkyl or halovinyl having one to three carbon atoms, $R_B$ is as defined broadly above, $R_1$ is $NH_2$, $R_2$ is OH and $R_3$–$R_5$ are all H;

X=CHOH, $R_A$=haloalkyl or halovinyl having one to three carbon atoms, $R_B$ is as defined broadly above, $R_1$ is $NH_2$, and A, $R_2$–$R_5$ are all H, except that neither $R_A$ nor $R_B$ can be $CF_3$;

X=CHOH, $R_A$=haloalkyl or halovinyl having one to three carbon atoms, $R_B$ is as defined broadly above, $R_1$ is $NH_2$, $R_2$ is OH and A, $R_3$–$R_5$ are all H, except that neither $R_A$ nor $R_B$ can be $CF_3$.

In all of the listed subsets of inhibitors, haloalkyl and halovinyl groups are preferably fluoroalkyl and fluorovinyl groups, respectively. In all of the listed subsets, $R_B$ is preferably H or a small alkyl group.

It is a specific object of the present invention to provide methods for inhibition of kynureninase which employ derivatives of α-amino-γ-hydroxy-γ-hydroxybenzene butanoic acids of the formula:

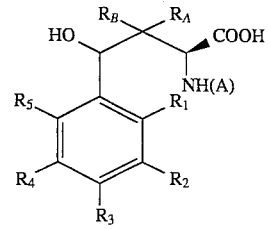

II wherein the stereochemical configuration at the α carbon is as indicated (and is the same configuration as the α-carbon in L-kynurenine), wherein $R_A$ is haloalkyl or halovinyl having from one to three carbon atoms, $R_B$ is H, or halogen, or a small alkyl, haloalkyl or halovinyl group each having one to three carbon atoms; $R_1$ is H, halogen, $NH_2$, $NR_6R_7$, $NO_2$, $CF_3$ or a small alkyl group having from one to three carbon atoms, with $R_6$ and $R_7$, independently of one another, being H, $CH_3$ or COH, wherein only one of $R_6$ or $R_7$ can be COH; $R_2$ is OH, H, halogen, $CF_3$, or a small alkyl group having from one to three carbon atoms; and $R_3$, $R_4$ and $R_5$, independently of one another, are H, OH, halogen, $CF_3$, $NO_2$, $NH_2$, or a small alkyl group having from one to three carbon atoms, except that neither $R_A$ nor $R_B$ can be $CF_3$. Inhibitors useful in the methods of this invention include the compounds of formula II in which the halogen of $R_1$–$R_5$ is fluorine, $R_2$ is H or OH, $R_1$ is $NH_2$ or H, and $R_A$, $R_B$, $R_3$, $R_4$ and $R_5$ are H or fluorine. More preferred inhibitors are those in which $R_1$ is $NH_2$ and $R_A$, $R_B$, $R_3$, $R_4$ and $R_5$ are H. $R_A$ is preferably a fluoroalkyl or fluorovinyl group. It is also preferred that for a fluoroalkyl group, there is at least one fluorine substituent on the carbon bound to the β-carbon of the inhibitor.

For inhibition of bacterial kynureninase it is preferred that $R_2$ is H. For inhibition of plant and animal kynureninase it is preferred that $R_2$ is OH.

It is a more specific object of this invention to provide methods of inhibition of kynureninase which are α-amino-γ-hydroxy-γ-aryl butanoic acids having the structure:

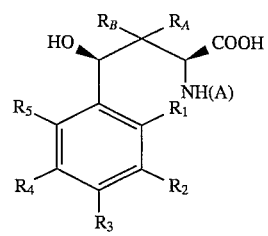

III wherein the configuration at the α carbon is the same as that of the α-carbon in L-kynurenine) and wherein A, $R_{1-7}$, $R_A$ and $R_B$ are as defined above for formulas I and II. Neither $R_A$ nor $R_B$ can be $CF_3$. For inhibition of bacterial kynureninase it is preferred that $R_2$ is H. When X is CO, it is contemplated that one of $R_A$ and $R_B$ will be a haloalkyl group, or one of $R_A$ and $R_B$ can also be a haloalkyl or a halovinyl group. Within this context, halogens can be fluorine or chlorine, among others. Generally fluorine is preferred to chlorine. Halovinyl groups can include $CF=CH_2$ and $CF=CF_2$ among others. Haloalkyl groups can include, among others $CF_3$, $CHF_2$, $CH_2F$, $CH_2CF_3$, $CH_2CHF_2$, $CH_2F$, $CHFCH_3$, $CF_2CH_3$, $CHFCHF_2$, $CF_2CHF_2$, $CHFCH_2F$, $CF_2CH_2F$, $CHFCF_3$, $CF_2CF_3$, $CH_2CH_2CF_3$, $CH_2CH_2CHF_2$ and $CH_2CH_2CH_2F$, and the like. Haloalkyl groups can also be one of $CF_3$, $CHF_2$, $CH_2F$, $CH_2CF_3$, $CH_2CH_2F$ and $CH_2CHF_2$. Alternatively, a haloalkyl group can be one of $CF_3$, $CH_2F$ and $CHF_2$. The haloalkyl groups set forth above can also further include the chlorinated homologues of any of the foregoing. It is preferred in that the haloalkyl group, there is at least one halogen substituent on the carbon bound to the β-carbon of the inhibitor. $R_1$–$R_5$ can be any of those set forth broadly above for formulas I and II. $R_1$=$NH_2$ is a preferred substitutent. For inhibition of plant and animal kynureninases it is preferred that $R_2$ is OH and $R_1$ is $NH_2$.

Salts of the compounds of formulas I–III are considered functional equivalents thereof with respect to inhibition of kynureninase. In particular, pharmaceutically acceptable salts of the compounds of formulas I–III are useful for the methods of the present invention and are useful in any therapeutic treatment of animals based on the inhibitory action of the compounds of formulas I–III.

This invention thus provides methods of inhibiting kynureninase in vitro and/or in vivo which comprises the step of contacting the enzyme with an inhibitory amount of one or more of the compounds of formulas I–III or salts, particularly pharmaceutically acceptable salts, thereof. It is well understood in the art that a precursor prodrug may be converted in vivo to a therapeutically active drug. Any such prodrug precursors of the compounds of formulas I–III are encompassed by this invention.

Therapeutic applications of the methods of the present invention relate particularly to inhibition of animal kynureninases, particularly those of mammals. Inhibitors in which $R_1$ is $NH_2$ and $R_2$ is OH are preferred for such therapeutic applications.

Compounds of the present invention that are preferred for therapeutic applications of the methods of the present invention are those that have minimal toxic or irritant effect toward the target of the therapy. If the inhibitor reacts with kynureninase, it is important that the product of that reaction be substantially nontoxic.

Kynureninases from different sources have different substrate preferences. For example, the preferred substrate of mammalian kynureninase is 3-hydroxy-L-kynurenine rather than L-kynurenine. In general, for a particular kynureninase, a preferred inhibitor of formula I–III will possess the phenyl ring substitutions of a preferred substrate of that kynureninase. Substrate preferences of kynureninases are known in the art or can be readily determined by routine experimentation.

A subset of inhibitors of formulas I–III particularly useful for inhibition of animal and plant kynureninases are those in which $R_1$=$NH_2$, $NO_2$, $CF_3$, halogen or $NR_6R_7$, and $R_2$=OH. Compounds of formulas I–III in which $R_1$=$NH_2$ and $R_2$=OH are more preferred for inhibition of animal and plant kynureninases.

DETAILED DESCRIPTION OF THE INVENTION

Kynureninases catalyze the hydrolysis of aryl-substituted γ-keto-α-amino acids. Kynureninase has been identified and isolated from certain bacteria, fungi, and yeasts as well as from mammalian sources. Kynureninases from different sources have been reported to have different substrate specificities. L-kynurenine is the preferred "natural" substrate of bacterial kynureninase. In contrast, for mammalian, yeast and fungal kynureninases, 3-hydroxy-L-kynurenine is the preferred "natural" substrate. This preference for 3-hydroxy-L-kynurenine, as assessed by relative substrate $K_m$'s, is characteristic of animal and plant kynureninases. The relative affinities of kynureninases for substrates other than L-kynurenine and 3-hydroxy-L-kynurenine can also depend on the source of the enzyme. Animal and plant kynureninases are sometimes called 3-hydroxykynureninases. The term kynureninase as used herein includes both bacterial, plant and animal kynureninases. Bacterial kynureninases are exemplified by the enzyme isolated from *Pseudomonas fluorescens*. Mammalian kynureninase is exemplified by the enzyme isolated from mammalian liver, in particular rat liver. A bacterial kynureninase will generally display substrate specificity like that of the *P. fluorescens* kynureninase. Mammalian kynureninase will generally display substrate specificity like that of rat liver kynureninase. Kynureninases, from all sources, catalyze the same types of reactions and so the mechanisms of the reactions they catalyze should be the same. Differences in affinities for substrates is believed to be associated with differences in the substrate binding site.

The present invention provides inhibitors of kynureninase. Some of these inhibitors are substrates of the enzyme, some are not substrates. Inhibitors of this invention may be competitive inhibitors of the enzyme for their natural substrates L-kynurenine and 3-hydroxy-L-kynurenine. Other kynureninase inhibitors of the present invention utilize the β-carbanion intermediate to activate a latent group, generating a highly reactive group within the active site of the enzyme, with resultant irreversible covalent modification. The prototype of this class of inactivators will be β-fluoromethylkynurenine. This class of inhibitors is characterized by the presence of a halogen substituent on the carbon of the group attached to the β-carbon of the inhibitor.

The proposed mechanism for irreversible inactivation of kynureninase by fluoromethylkynurenin and related compounds is shown in Scheme I. Elimination of HF from the β-carbanion intermediate will generate an α,β-unsaturated imine, a strongly electrophilic agent, which will undergo Michael reaction with an active site nucleophile to give a covalently-modified, irreversibly inactived kynureninase. γ-Fluoroamino acids have been shown to inactivate γ-cystathionase, a PLP-dependent enzyme which is known to generate a β-carbanion intermediate (Alston et al. (1981) *FEBS Letts.* 128: 293).

SCHEME I
Mechanism of Inactivation of Kynureninase by β-fluoromethylkynurenine

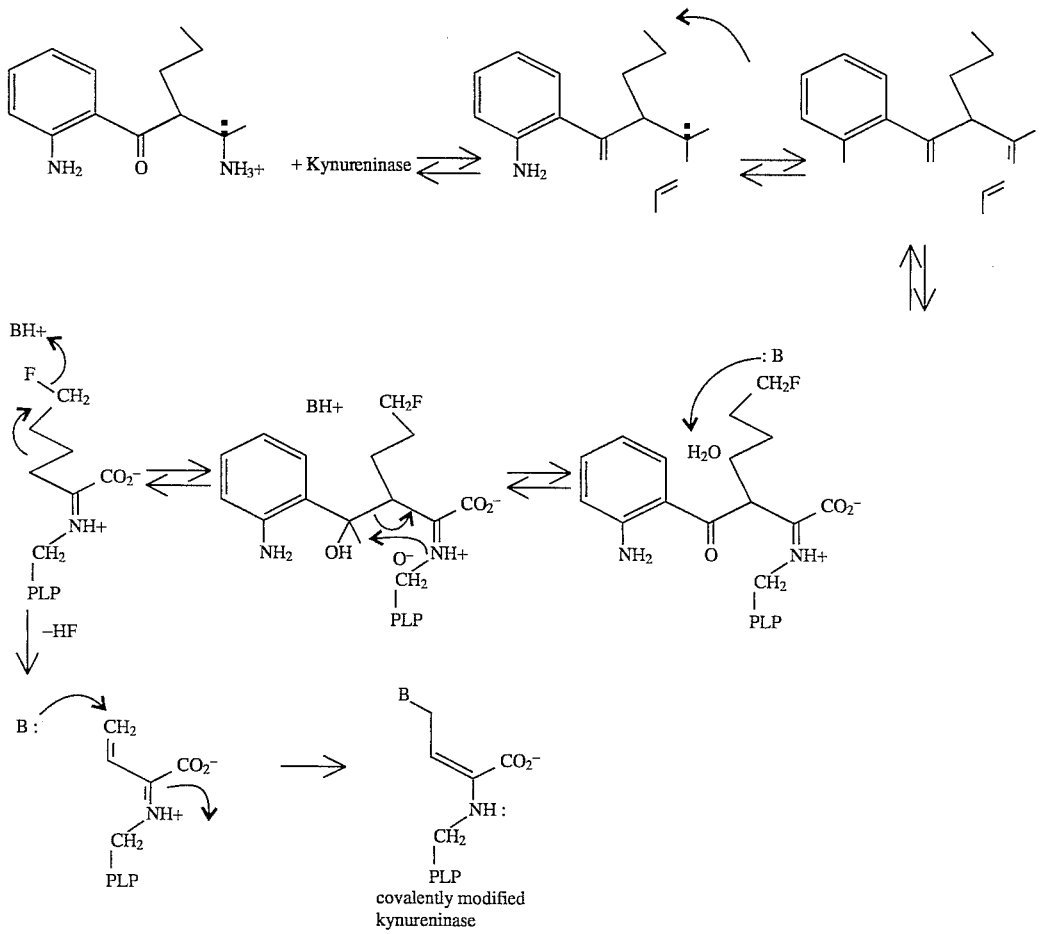

Inhibition, as used herein, refers to inhibition of the hydrolysis of L-kynurenine and/or 3-hydroxy-L-kynurenine. Competitive inhibition and noncompetitive inhibition can be assessed by in vitro methods well-known in the art. Preferred inhibitors of a particular kynureninase are those having a $K_i$ less than or equal to the $K_m$ of the preferred substrate either L-kynurenine or 3-hydroxy-L-kynurenine for that kynureninase. Most preferred inhibitors of this invention mediate the irreversible inhibition of kynureninase. In general for irreversible inhibitors, it is preferred that the inhibitor have an affinity sufficiently high so as to result in an inhibition of a desired proportion of kynureninase activity, as will be readily apparent to the skilled artisan. The level of inhibition that is achieved is dependent on the concentration of inhibitor in the vicinity of the enzyme. In general, the higher the affinity of the enzyme for the inhibitor, the more potent an inhibitor is. For applications of the methods of inhibition of kynureninase, particularly therapeutic applications, it is generally preferred to employ high affinity (low $K_i$) inhibitors to minimize the amount of inhibitor that must be administered.

Kynureninases are known to catalyze other reactions, for example, cysteine conjugate β-lyase activity. Inhibition of kynureninases can also be, at least qualitatively, assessed employing in vitro assays for such alternate kynureninase activities.

The aldol reaction of L-kynurenine and benzaldehyde catalyzed by kynureninase was found to proceed to give predominantly (80%) the (αS, γR) diastereomer of α-amino-γ-hydroxybenzenebutanoic acid.

The stereospecificity of the aldol reaction, as well as the results of Bild and Morris, Arch. Biochem. Biophys. (1984) 235:41–47, supports a general base mechanism for kynureninase, as shown in Scheme I. The stereospecificity for cleavage of the (4R)-isomer is likely a reflection of favorable orientation for the active site general base to initiate the retro-aldol cleavage by proton abstraction (Scheme IIA).

The basic group involved is probably the carboxylate that Kishore (1984) supra reported is modified by suicide substrate inhibitors. Although Kishore proposed that this carboxylate is responsible for α-proton abstraction, stereochemical studies by Palcic et al., J. Biol. Chem. (1985) 260:5248–5251, found that an α-proton of kynurenine is scrambled between the α- and β-positions of the L-alanine product, and thus the proton abstraction at the α-C is probably due to a polyprotic base, most likely a lysine ε-amino group. In the hydrolysis of L-kynurenine, the second general base would be required to assist in hydration of the ketone, by abstraction of a proton from a water molecule (Scheme IIB). The observed stereochemistry of the aldol-reactions suggests that the water attacks on the reface of the carbonyl group, giving the (S)-gem-diolate anion. Subsequent rapid collapse of this tetrahedral intermediate is likely and would generate the enzyme-bound enamine of PLP-L-alanine and anthranilic acid (Scheme IIB). In the case of the (4S)-isomer, the carbinol group would mimic this gem-diol tetrahedral intermediate, but is not oriented in a position favorable for the retro-aldol reaction to occur. Thus, this compound is a "transition-state analogue," and would be expected to bind to kynureninase very tightly.

Although not wishing to be bound by any specific theory, it is believed that the inhibitors of the present invention represent "transition-state analogue" inhibitors of kynureninase in view of the newly proposed mechanism of Scheme I. Based on this proposed mechanism, α-amino-γ-hydroxybenzenebutanoic acids having electron-withdrawing groups, including but not limited to, $CF_3$, halogen, $NO_2$, CN, etc.,

SCHEME II

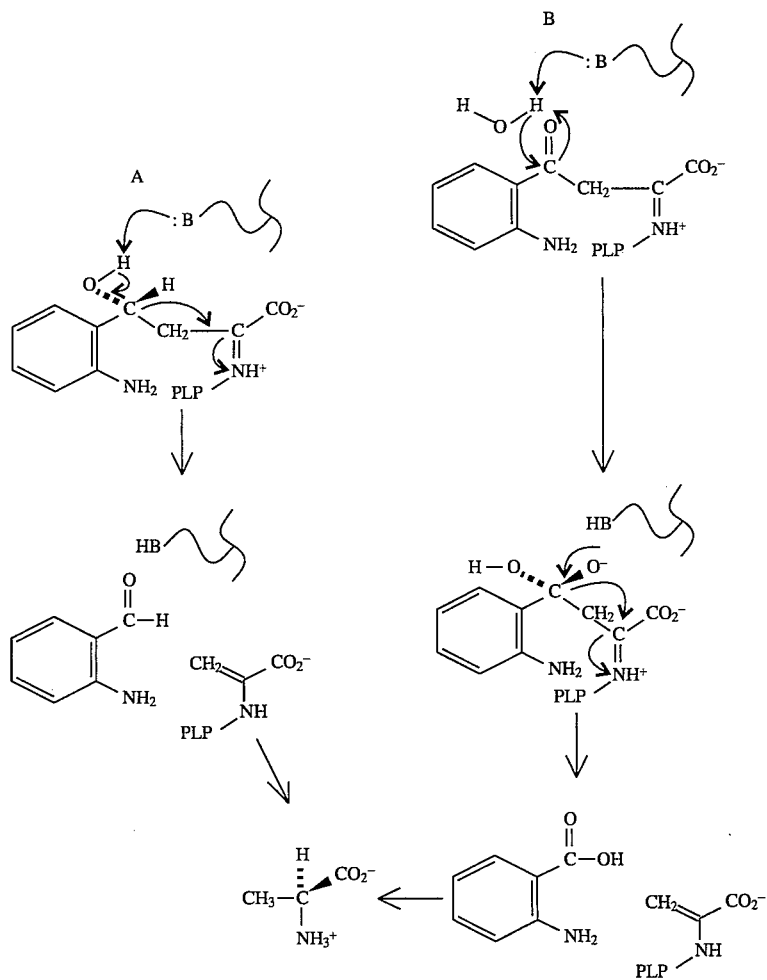

As an extension of these mechanistic studies, the reactivities of dihydrokynurenine diastereomers were examined. (αS,γR)-Dihydrokynurenine ((αS,γR)-α,2-diamino-γ-hydroxybenzenebutanoic acid) was found to be a slow substrate for the retro-aldol cleavage reaction catalyzed by kynureninase, while the analogous (αS,γS) diastereomer was unreactive. When these compounds were included in reaction mixtures of enzyme and L-kynurenine, the reaction was strongly inhibited. Analysis of the kinetic data in the presence of various concentrations of the dihydrokynurenines demonstrated that they act as competitive inhibitors with respect to kynurenine, with $K_i$ values of 1.4 μM for the (αS,γS)-isomer and 5 μM for the (αS,γR)-isomer. These can be compared to the $K_m$ for L-kynurenine of 25 μM as measured in the present work, and indicate that (αS,γS)-dihydrokynurenine binds more tightly than does L-kynurenine. This increased affinity of (αS,γS)-dihydrokynurenine is characteristic of mechanism-based, or "transition-state analogue" inhibitors.

appropriately substituted on the benzene ring to stabilize the proposed "transition state" will act as inhibitors of the kynureninase.

The kynureninase inhibitors of the present invention can be prepared as exemplified for the preparation of fluoromethylkynurenines shown in Scheme III, using well-known chemical reactions. Fischer indole cyclization adds the β-fluoromethyl side chain. The indole ring of the resultant β-fluoromethyltryptophan is readily cleaved by ozonolysis to give the desired β-fluoromethylkynurenine. A mixture of racemic diastereomers of β-fluoromethylkynurenine is obtained, that is readily separable by known techniques such as by preparative HPLC (Phillips and Dua (1991), supra). 3-Hydroxykynurenine analogues can be prepared by substituting σ-methoxyphenylhdrazine for phenylhydrazine (second step in III). A wide range of other latent reactive functionalities can be incorporated onto the β-position of kynurenine or 3-hydroxykynurenine, and these analogues will inactivate kynureninase via mechanisms similar to that shown in Scheme I.

Various inhibitors of this invention can be synthesized, without the expense of undue experimentation, by methods analogous to Scheme III by the appropriate selection of starting materials, e.g., selection of appropriate R groups and substituted phenylhydrazines, and using art-known chemical reactions and techniques. For example, compounds produced by the procedure of Scheme III can be reduced, for example, using sodium borohydride to give the analagous compound having CHOH rather than CO at the γ position. N-acetyl derivatives of the compounds of the present invention can be readily prepared from corresponding amines employing well-known techniques. Such alterations to achieve desired inhibitors are within the skill of the art and can be accomplished without expense of undue experimentation.

EXAMPLES

Example 1

Investigation of the Mechanism of Kynureninase-catalyzed adol-reactions

Bacterial kynureninase was prepared from cells of *Pseudomonas fluorescens* (ATCC 11250, for example) essentially as described by Hayaishi and Stanier (1952) J. Biol. Chem. 195:735–740. Cells were grown on a minimal medium containing 0.1% L-tryptophan as the sole carbon and nitrogen source.

From 100 l of medium, grown for 18 h at 30° C., 230 g of wet cell paste was obtained. The cells were suspended in 1 l of 0.01M potassium phosphate, pH 7.0, and disrupted by 2 passages through a Manton-Gaulin homogenizer. After

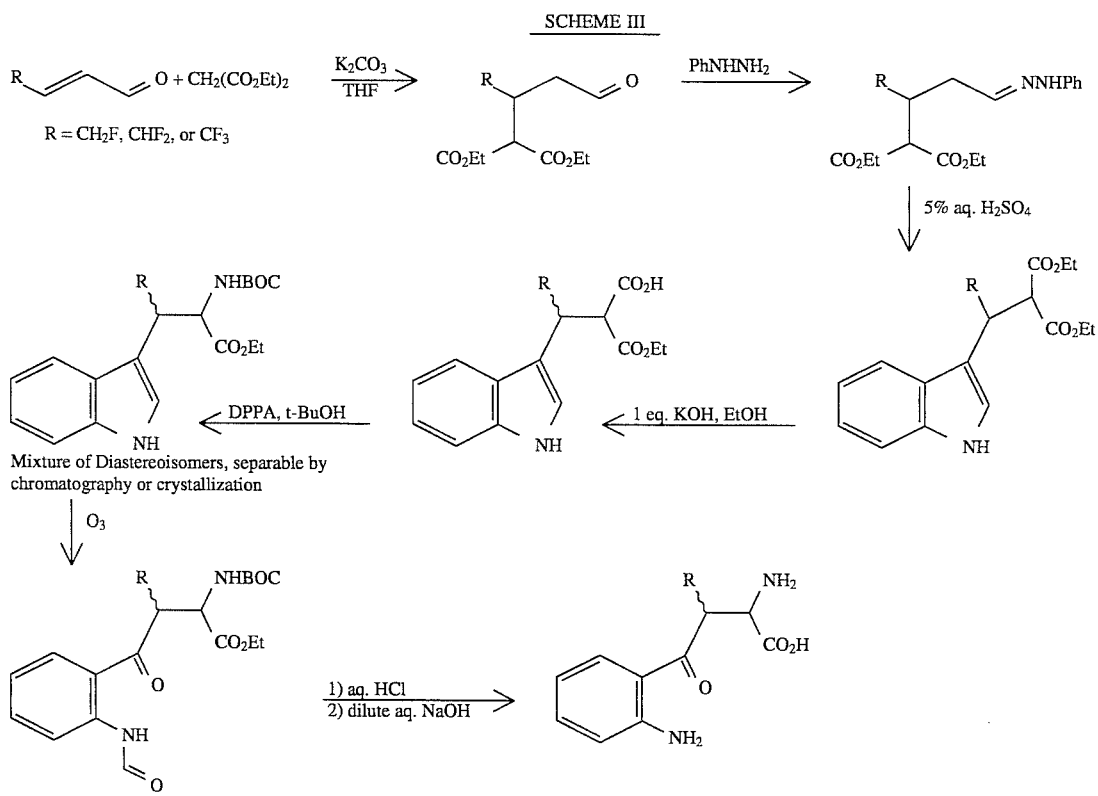

SCHEME III

As has been described herein, one of the pair of diastereomers in cases, in which diastereomers can exist, will be a preferred kynureninase inhibitor. It will be appreciated, however, that inhibition can be obtained by use of a mixture of the diastereomers. In order to obtain maximal inhibition for the amount of inhibitor employed, it will be preferable to maximize the amount of the more inhibitory diastereomer in the mixture.

Those of ordinary skill in the art will understand that alternative or equivalent methods, procedures, techniques and assays other than those specifically described herein can be readily employed or adapted to achieve the objects of this invention. All such alternative and equivalents are encompased by this invention. The scope of this invention is not limited by the specific examples herein which are intended to illustrate the invention.

centrifugation of the cell extract for 1 h at 10,000×g, the enzyme was partially purified by ion-exchange chromatography on DEAE-cellulose and ammonium sulfate precipitation. The preparation used in the results of Table 1 exhibited a specific activity of 0.2 μmol min$^{-1}$ mg$^{-1}$.

L-kynurenine and benzaldehyde (in excess) were incubated with kynureninase under the conditions described by Bild and Morris (1984) Arch. Biochem. Biophys. 235:41–47, which is incorporated by reference herein. The product of this reaction was purified by preparative HPLC and identified as α-amino-γ-hydroxybenzenebutanoic acid. This product was produced in quantitative yield based on L-kynurenine.

The α-amino-γ-hydroxybenzenebutanoic acid produced in the kynureninase reaction exhibited a negative CD (circular dichroism) extremum at 260 nm, with vibronic splitting characteristic of a chirally substituted benzoyl alcohol chromophore. Based on a comparison of the CD spectra of the product with those of (R)- and (S)-mandelic acids, the predominant chiral product was determined to have the same absolute configuration as (S)-mandelic acid and thus to have the (γR)-configuration. (The terms R and S are employed as is conventional according to the Cahn-Ingold-Prelog rules.) NMR analysis (300 MH$_z$ $^1$H) of the product demonstrates that it is an 80:20 mixture of (αS,γR):(αS,γS) diastereomers of α-amino-γ-hydroxybenzene butanoic acid.

Example 2

Reactivity of Dihydrokynurenine with Kynureninase

L-kynurenine (from commercial sources) was reduced with NaBH$_4$ in H$_2$O to give dihydrokynurenine [α,2-diamino-γ-hydroxybenzenebutanoic acid]. The progress of reaction was monitored by the disappearance of the 360 nm UV absorption band of L-kynurenine. The reduction resulted in a 60:40 mixture of diastereomers. The diastereomers were separated by preparative HPLC on a 20×250 mm C18 column (Rainin, Dynamax) eluting with 0.1% acetic acid (5 ml/min). The first peak to elute from the HPLC column was identified by $^1$H NMR analysis to be the (αS,γS)-diastereomer. The second peak to elute was identified by $^1$H NMR analysis to be the (αS,γR)-diastereomer.

The CD spectra of the separated dihydrokynurenine diastereomers were consistent with this identification.

The reactivity of the two dihydrokynurenines with kynureninase in 0.1M potassium phosphate buffer, pH 8.0, at 25° was examined. Reaction was followed by the appearance of o-aminobenzaldehyde, as determined spectrophotometrically by the increase in absorbance at 360 nm (See Tanizawa and Soda (1979) *Biochem.* (Tokyo) 86:1199–1209, which is incorporated by reference herein).

The (αS,γR)-dihydrokynurenine diastereomer reacted slowly with kynureninase to produce o-aminobenzaldehyde. No significant reaction of the (αS,γS)-diastereomer was detected. Tanizawa and Soda (1979) supra had reported that dihydrokynurenine reacted with kynureninase with a V$_{max}$ of about 65% that of L-kynurenine. In contrast, the present work indicates that only the (αS,γR)-diastereomer of dihydrokynurenine reacts, only at about 5% of the rate of L-kynurenine. Under the conditions employed and with the bacterial kynureninase prepared as described in Example 1, K$_m$ of the reaction of L-kynurenine was determined to be 25 μM. This value is similar to the K$_m$ of 35 μM for L-kynurenine obtained by Tanizawa and Soda.

Example 3

Inhibition of Kynureninase by Dihydrokynurenine

Inhibition of kynureninase by dihydrokynurenine was measured by including the potential inhibitor in the enzyme assay mixture (see Example 1 and Tanzawa and Soda (1979) supra) and determining the apparent Km for L-kynurenine (the preferred substrate of bacterial kynurenine) in the absence and presence of the potential inhibitor. K$_i$ values were then calculated using the standard equation:

$$(K_m)_{app} = K_m(1 + [I]/K_i)$$

where [I] is the molar concentration of inhibitor and K$_m$=25 μM.

Inhibition of kynureninase by the (αS,γR)- and (αS,γS)-diastereomers of dihydrokynurenine was examined and K$_i$'s were determined. Both compounds strongly inhibited the reaction of kynureninase with L-kynurenine. K$_i$ values of 1.4 μM for the (αS,γS)-diastereomer and 5 μM for the (αS,γR) diastereomer were measured. Both compounds were found to be competitive inhibitors of kynureninase.

Inhibition of mammalian kynureninase can be measured using several different assays for enzyme activity. Rat liver kynureninase is obtained from homogenization of rat liver, followed by precipitation with (NH$_4$)$_2$SO$_4$, as described by Stevens, J. L., J. Biol. Chem. (1985) 260:7945–7950, which is incorporated by reference herein. The activity of rat liver kynureninase was assessed by measurement of the cysteine conjugate β-lyase activity, as described by Stevens (supra), with S-(2-benzothiazolyl)cysteine, a nonphysiological chromophoric substrate. Inhibition of kynureninase by the dihydrokynurenine diastereomers was assessed with respect to reaction with that substrate.

Both the (αS,γR) and (αS,γS) diastereomers of dihydrokynurenine were found to inhibit the reaction of rat liver kynureninase. The (αS,γS) diastereomer was found to be the stronger competitive inhibitor with K$_i$ under the assay conditions of about 690 μM.

Example 4

Competitive Inhibition of Kynureninase by Compounds (I, II and III)

Kynureninase activity is measured at 25° C. by following the decrease in absorbance at 360 nm (ε=−4500M$^{-1}$ cm$^{-1}$). A typical assay mixture contained 0.4 mM L-kynurenine in 0.04M potassium phosphate, pH 7.8, containing 40 μM pyridoxal-5'-phosphate, at 25° C. The effects of the β-substituted inhibitors of the present invention are analyzed by making obvious modifications of this protocol and with varying concentrations of inhibition and/or substrate using art-known principles and methods.

We claim:

1. An inhibitor of kynureninase having the formula:

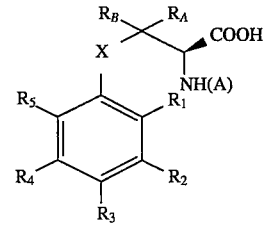

wherein:

R$_A$ is a haloalkyl group or halovinyl group having one to three carbon atoms, and R$_B$ is H, or a halogen, or a small alkyl, haloalkyl or halovinyl group each having one to three carbon atoms, except that neither R$_A$ nor R$_B$ can be CF$_3$ when X=CHOH;

X is CO or CHOH;

A is H or an acetyl group;

R$_1$ is H, NH$_2$, NR$_6$R$_7$, NO$_2$, halogen, CF$_3$ or a small alkyl group having from one to three carbon atoms, wherein:

R$_6$ and R$_7$, independently of one another, are H a formyl group or a small alkyl group having from one to three carbon atoms with the exception that only one of R$_6$ or R$_7$ can be a formyl group;

$R_2$ is OH, H, halogen, $CF_3$ or a small alkyl group having from one to three carbon atoms;

$R_3$, $R_4$ and $R_5$, independently of one another, are H, OH, halogen, $CF_3$, $NO_2$, $NH_2$ or small alkyl group having from one to three carbon atoms; and pharmaceutically acceptable salts thereof.

2. The inhibitor of claim 1 wherein X is CO.
3. The inhibitor of claim 2 wherein $R_1$ is $NH_2$.
4. The inhibitor of claim 1 wherein X is CHOH.
5. The inhibitor of claim 4 wherein $R_1$ is $NH_2$.
6. The inhibitor of claim 1 wherein $R_1$ is $NH_2$ and $R_2$ is OH.
7. The inhibitor of claim 1 wherein A is H.
8. The inhibitor of claim 1 which has the formula:

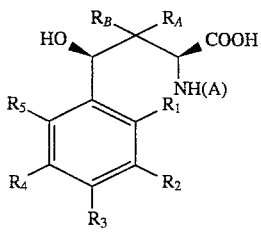

and pharmaceutically acceptable salts thereof.

9. The inhibitor of claim 8 wherein:

$R_A$ is a haloalkyl group and $R_B$ is one of H or F;

$R_1$ is $NH_2$, H or F;

$R_2$ is OH, H or F; and $R_3$, $R_4$ and $R_5$, independently of one another, are H or F.

10. The inhibitor of claim 9 wherein $R_1$ is $NH_2$.
11. The inhibitor of claim 10 wherein $R_2$ is H.
12. The inhibitor of claim 10 wherein $R_2$ is OH.
13. The inhibitor of claim 2 wherein:

$R_A$ is a haloalkyl group having one to three carbons and $R_B$ is one of H or F.

14. The inhibitor of claim 2 wherein $R_B$ is H or a small alkyl having one to three carbon atoms.
15. The inhibitor of claim 14 wherein $R_A$ is a fluoroalkyl group.
16. The inhibitor of claim 15 wherein $R_A$ is an α-fluoroalkyl group.
17. The inhibitor of claim 9 wherein said kynureninase is a mammalian kynureninase, and in said compound $R_1$ is $NH_2$ and $R_2$ is OH.
18. A method for inhibiting kynureninase which comprises the step of contacting said kynureninase with an inhibiting amount of a compound of claim 1 or a mixture of compounds of claim 1.

* * * * *

UNITED STATES PATENT AND TRADEMARK OFFICE
CERTIFICATE OF CORRECTION

PATENT NO.   : 5,495,044

DATED        : February 27, 1996

INVENTOR(S)  : Robert S. Phillips; Lakshmi V. Cyr

It is certified that error appears in the above-identified patent and that said Letters Patent is hereby corrected as shown below:

At column 8, line 57, please replace "fluoromethylkynurenin" with --fluoromethylkynurenine--.

At columns 9 and 10, please replace Scheme I with new page Scheme I shown on the following page.

UNITED STATES PATENT AND TRADEMARK OFFICE
CERTIFICATE OF CORRECTION

PATENT NO. : 5,495,044

DATED : February 27, 1996

INVENTOR(S) : Robert S. Phillips; Lakshmi V. Cyr

SCHEME I
Mechanism of Inactivation of Kynureninase by β-fluoromethylkynurenine

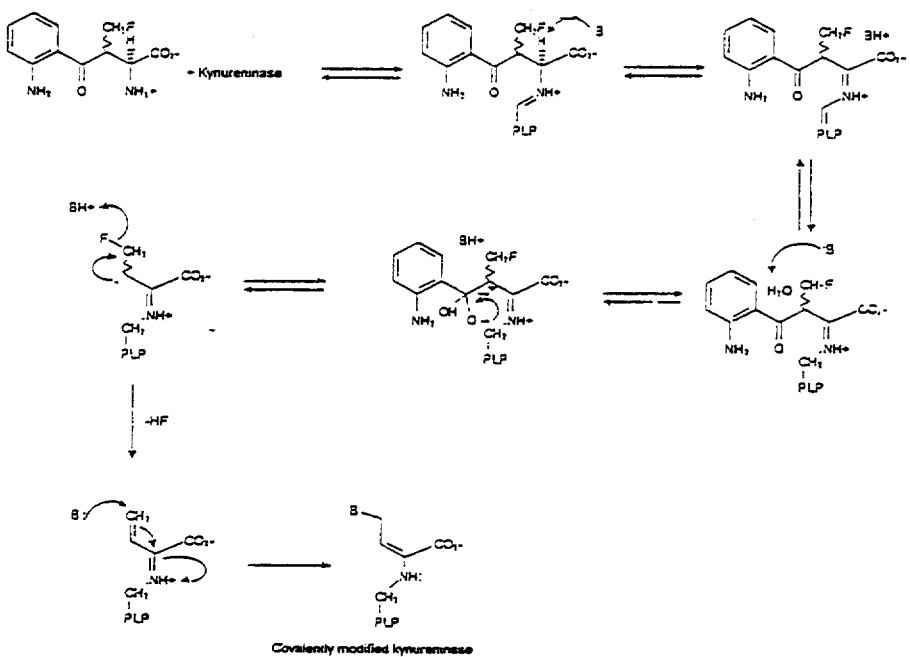

Signed and Sealed this

Ninth Day of July, 1996

Attest:

BRUCE LEHMAN

*Attesting Officer*  *Commissioner of Patents and Trademarks*